US010729836B2

(12) United States Patent
Golaszewski et al.

(10) Patent No.: US 10,729,836 B2
(45) Date of Patent: Aug. 4, 2020

(54) METHOD AND APPARATUS FOR PREMIXING DIALYSATE

(71) Applicant: B. BRAUN AVITUM AG, Melsungen (DE)

(72) Inventors: Grzegorz Golaszewski, Lohfelden (DE); André Wagner, Kassel (DE)

(73) Assignee: B. BRAUN AVITUM AG, Melsungen (DE)

(*) Notice: Subject to any disclaimer, the term of this patent is extended or adjusted under 35 U.S.C. 154(b) by 519 days.

(21) Appl. No.: 15/703,347

(22) Filed: Sep. 13, 2017

(65) Prior Publication Data

US 2018/0085511 A1    Mar. 29, 2018

(30) Foreign Application Priority Data

Sep. 26, 2016 (DE) .......................... 10 2016 118 172

(51) Int. Cl.
*A61M 1/16* (2006.01)
*A61K 33/00* (2006.01)
(Continued)

(52) U.S. Cl.
CPC ........... *A61M 1/1656* (2013.01); *A61K 33/00* (2013.01); *A61M 1/1607* (2014.02);
(Continued)

(58) Field of Classification Search
CPC .. A61M 1/16; A61K 33/00; B01F 3/08; B01F 5/02; B01F 15/00; G01N 27/06
See application file for complete search history.

(56) References Cited

U.S. PATENT DOCUMENTS 4,399,036 A * 8/1983 Babb .................. A61M 1/1656
210/638
6,991,190 B2 1/2006 Lortz et al.
(Continued)

FOREIGN PATENT DOCUMENTS

DE          10214699 A1    10/2003
DE      102014015858 A1     4/2016
(Continued)

OTHER PUBLICATIONS

German Search Report for German Application No. 10 2016 118 172.2, with translation, dated May 15, 2017—16 Pages.
(Continued)

*Primary Examiner* — Tatyana Zalukaeva
*Assistant Examiner* — Ilya Y Treyger

(57) ABSTRACT

An apparatus for premixing fluids to form dialysate for an extracorporeal blood treatment includes at least a first feed portion for supplying at least a first fluid from at least a first fluid reservoir, at least a second feed portion for supplying at least a second fluid from at least a second fluid reservoir, a premixing portion being configured to premix fluids supplied via the feed portions in counter flow to form a fluid mixture and at least one drain portion for draining the fluid mixture premixed in the premixing portion as dialysate. A method carries out appropriate steps. In a conductivity measurement along the drain portion the conductivity of the premixed fluid mixture is measured by means of a digital filter adapted to be parameterized based on at least two state variables of the premixing process at least in two phases with a first predictive phase and a second corrective phase.

8 Claims, 2 Drawing Sheets

(51) Int. Cl.
    *B01F 3/08*         (2006.01)
    *B01F 5/02*         (2006.01)
    *B01F 15/00*       (2006.01)
    *G01N 27/06*       (2006.01)

(52) U.S. Cl.
    CPC .......... *B01F 3/0873* (2013.01); *B01F 5/0256* (2013.01); *B01F 15/00227* (2013.01); *G01N 27/06* (2013.01); *A61M 2205/3317* (2013.01); *A61M 2205/50* (2013.01); *B01F 2215/0034* (2013.01)

(56) References Cited

U.S. PATENT DOCUMENTS

| | | | |
|---|---|---|---|
| 9,354,193 B2 * | 5/2016 | Platte | G01N 27/07 |
| 2005/0011833 A1 | 1/2005 | Stahl | |
| 2013/0274642 A1 | 10/2013 | Soykan et al. | |
| 2014/0107835 A1 | 4/2014 | Biasi et al. | |
| 2017/0304519 A1 | 10/2017 | Jonas et al. | |

FOREIGN PATENT DOCUMENTS

| | | |
|---|---|---|
| EP | 1491222 A1 | 12/2004 |
| EP | 2281626 A2 | 2/2011 |

OTHER PUBLICATIONS

Extended European Search Report for European Application No. 17 188 239.2, dated May 29, 2018, with English translation, 19 pages.
European Partial Search Report for European Application No. 17188239.2, dated Feb. 14, 2018 with translation, 28 pages.

* cited by examiner

METHOD AND APPARATUS FOR PREMIXING DIALYSATE

CROSS REFERENCE TO RELATED APPLICATIONS

This application claims priority to German application DE 10 2016 118 172.2 filed Sep. 26, 2016, the contents of such application being incorporated by reference herein.

FIELD OF THE INVENTION

The invention relates to a method and an apparatus for mixing dialysate in advance and in particular relates to a method and an apparatus for premixing dialysate in an apparatus for extracorporeal blood treatment including subsequent conductivity measurement of the premixed dialysate.

BACKGROUND OF THE INVENTION

During extracorporeal blood treatment, for example dialysis, due to a concentration gradient between the blood and the dialysate, a diffusive transport process takes place between the blood and the dialysate.

Said diffusive transport process is substantially important for small-molecular uremia toxins diffusing into the toxin-free dialysate depending on their concentration in the blood and for electrolytes and buffer substances that have either to be removed from the blood (potassium, phosphate) or to be added to the blood (calcium, buffer). The level of concentration of the electrolytes and the buffers in the dialysate determines the rate of the diffusion through the dialysis membrane. The selection of the dialysate composition allows to influence and adapt the diffusion process.

Dialysate is required in large quantity. In the case of dialysate flow of e.g. 500 ml/min, the dialysate quantity for a four to five hours' dialysis treatment amounts to approx. 120 to 150 liters. The dialysate is produced by diluting concentrate with purified osmotic water. The possibility of varying the dialysate composition by specific admixture of individual components permits a dialysis treatment which is tailored to individual needs of the patient.

For use in hemodialysis, dialysates have to be provided which are adapted as properly as possible in the physiological respect, i.e. which have a pH value of about 7.4, contain essential electrolytes and further include a buffer system which is physiological and is suited for adjusting the desired pH value. Since bicarbonate also represents the physiological buffer of blood, generally bicarbonate is used as a buffer system.

In an apparatus for extracorporeal blood treatment, for example a dialysis machine, a so-called dialysate block (DF block) serves as components or parts carrier for, inter alia, conductivity probes and temperature sensors of the dialysate preparation. Usually, principal components of the dialysate preparation are at least one bicarbonate pump and at least on concentrate pump comprising various conductivity measuring cells as well as at least one flow pump. Bicarbonate concentrate admixed via the bicarbonate pump is combined in a mixing chamber and is measured by a conductivity measuring cell. The concentrate or acid concentrate is mixed according to the same principle and is measured by a further conductivity measuring cell.

Temperature sensors are responsible for temperature compensation of the conductivity measurement. The temperature detection of a first temperature sensor is performed after adding cold concentrate (recording of second measured value for the temperature system) and the temperature detection of a second temperature sensor (and of a third temperature sensor) is performed directly ahead of the dialyzer and thus serves for compensating temperature losses.

The conductivity measuring cell or probe is an independently operating monitoring unit. The temperature compensation is performed via a further temperature sensor.

If proportioning is carried out in an apparatus for extracorporeal blood treatment, such as a dialysis machine, with check valves and mixing chambers so as to be capable of using an evaluation of measuring signals of the conductivity probes, permeate and concentrates have to be mixed in a complicated manner in mixing chambers, as the conductivity is measured immediately after admixing the concentrates, so as to obtain an evaluable signal by a previously utilized low-pass filter algorithm.

Moreover, a known solution for measuring the conductivity signal in the apparatus requires a large surface area and/or space and the manufacture of the mixing chambers and of the check valves involves high production and assembly costs.

SUMMARY OF THE INVENTION

Therefore, the object underlying the invention is to provide an apparatus for mixing concentrates and/or osmotic water in advance for an extracorporeal blood treatment which, on the one hand, prevents outgassing of the concentrates and is arranged to premix the concentrates in favor of obtaining a required mixing degree at the dialyzer.

Moreover, a robust filter algorithm is to be provided by which a conductivity measuring signal derived from a premixed concentrate can be evaluated.

In accordance with the invention, this object will be achieved by an apparatus and a method comprising the features of the independent claims. Advantageous developments of the invention are the subject matter of the enclosed subclaims.

A general idea underlying the invention is to prevent outgassing of concentrates and to premix concentrates and osmotic water and then to measure the conductivity of the premixed dialysate with a digital filter. Since the degree of mixing of the dialysate upon supply to the conductivity probes is still insufficient and cannot be measured by the currently known filter algorithms, furthermore a more robust filter algorithm is provided so as to be able to evaluate the conductivity measuring signal.

According to the general idea, the invention makes use of a constant primary pressure generated by the water column, before the concentrates are supplied, which primary pressure prevents the concentrates from outgassing. The mixing of the concentrates and of the osmotic water is performed by a counter flow principle. By measuring the conductivity at the dialyzer, it was found that the degree of mixing is sufficient without any check valves and mixing chambers via the components present in the dialysate system.

In order to be able to safely predict the mixing degree at the dialyzer and since the conductivity value is controlled in a digital manner, a digital filter is used which especially satisfies the requirements resulting from the dynamic nature of the mixing processes.

Since the mixing of permeate and concentrates has to be carried out within very short time, the mixing is carried out by the counter flow principle so as to obtain the required degree of mixing at the dialyzer coupling. Mixing is carried out within very short time and with a (controlled) small volume of the liquids to be mixed. Moreover, it is carried out turbulently with swirls resulting therefrom which result in thorough mixing.

According to aspects of the invention, advantages are resulting to the effect that no check valves are required for preventing the concentrates from outgassing, no mixing chamber is required for proportioning, the surface area and/or space occupied by the dialysate block can be saved, assembly operations are facilitated by omission of the dialysate block, hot plate welding processes for manufacturing the cost-intensive dialysate block are dropped, a liquid volume to be processed is significantly reduced, due to turbulent mixing by the counter flow principle short mixing times of the concentrates and of the permeate are obtained and the basic structure of the apparatus for extracorporeal blood treatment and, respectively, of the dialysis machine is maintained. Of further advantage are an easily applicable filtering technique for strongly turbulent signal forms, short delay times and little calculation effort due to the simple algorithm, the dispensability of a state model of the relevant system and a covariance matrix, easy implementation and parameterization and the representability of a stable and reliable conductivity control.

In detail, the object is achieved by an apparatus for premixing fluids to form dialysate for extracorporeal blood treatment containing at least a first feed portion for supplying at least a first fluid from at least a first fluid reservoir; at least a second feed portion for supplying at least a second fluid from at least a second fluid reservoir; a premixing portion which is configured to premix fluids supplied via the feed portions in counter flow to form a fluid mixture; and at least one drain portion for draining the fluid mixture premixed in the premixing portion as the dialysate.

Preferably, the first fluid is osmotic water and the second fluid is a concentrate of a substance to be used for extracorporeal blood treatment, further preferred a bicarbonate concentrate.

Preferably, in the at least one drain portion a fluid column for generating a constant primary pressure is provided which is configured to prevent at least one of the supplied fluids from outgassing.

Preferably, the at least one first feed portion and the at least one second feed portion are arranged on the outside relative to the apparatus and the drain portion is arranged between the at least one first feed portion and the at least one second feed portion and are communicated with the premixing portion in a fluid-guiding manner so that the at least one first fluid flows into the premixing portion from a first direction and the at least one second fluid flows into the premixing portion from a second direction, and the at least one first feed potion and the at least one second feed portion adopt a predetermined angle relative to each other which is configured so that the counter-flow premixing of the fluids in the premixing portion is generated in a turbulent and automatic manner based on flow.

Preferably, at least one conductivity measuring device along the drain portion is provided to measure the conductivity of the premixed fluid mixture and to generate a conductivity measuring signal capable of being further processed.

Preferably, the at least one conductivity measuring device comprises a digital filter adjustable based on at least two state variables of the premixing process, wherein one of the state variables can be derived from the respective other one and the digital filter is configured to be at least two-phase including a first predictive phase in which a closest system state is determined by way of measured values and a second corrective phase in which the preceding determining is corrected by way of previous values.

Preferably, the two state variables form a state vector $$v = \frac{dy}{dt} = \hat{y} \tag{1}$$

wherein y represents a position and v represents a velocity and the first and second phases of the filter are determined by the equations:

$$\hat{y}_{t+1} = \hat{y}_t + \Delta T \cdot \hat{v}_t \tag{2}$$

$$\hat{v}_{t+1} = \hat{v}_t \tag{3}$$

$$\hat{y}_t = \hat{y}_{t-1} + \alpha \cdot (y_t - \hat{y}_{t-1}) \tag{4}$$

$$\left| \hat{v}_t = \hat{v}_{t-1} + \frac{\beta}{\Delta T} \cdot (y_t - \hat{y}_{t-1}) \right. \tag{5}$$

wherein the equations (2) and (3) represent the predictive phase and the equations (4) and (5) represent the corrective phase, the variables in the equations represent estimates of the respective measured variable and the scanning time between two successive measurements, the index t indicates the current value with respect to the current measurement, the index t−1 indicates the value with respect to the respective last measurement, the index t+1 indicates the value with respect to the respective next measurement and filter characteristics are adjustable with a parameter $\alpha$ and a parameter $\beta$.

In detail the object is moreover achieved by a method for premixing fluids to form dialysate for an extracorporeal blood treatment, comprising the steps of: supplying at least a first fluid from at least a first fluid reservoir via at least a first feed portion; supplying at least a second fluid from at least a second fluid reservoir via at least a second feed portion; premixing the fluids supplied via the feed portions in counter flow to form a fluid mixture in a premixing portion; and draining the fluid mixture premixed in the premixing portion as a dialysate via at least one drain portion.

Preferably, the method further comprises performing a conductivity measurement along the drain portion for measuring the conductivity of the premixed fluid mixture for generating a conductivity measuring signal capable of being further processed, wherein the conductivity measurement is performed with a digital filter which is adjustable on the basis of at least two state variables of the premixing process, wherein one of the state variables can be derived from the respective other one and the digital filter is configured to be at least two-phase having a first predictive phase in which a next system state is determined by way of measured values and having a second corrective phase in which the preceding determining is corrected by way of previous values, and wherein the two state variables form a state vector $$v = \frac{dy}{dt} = \hat{y} \tag{1}$$

wherein y represents a position and v represents a velocity, and the first and second phases of the filter are determined by the equations:

$$\hat{y}_{t+1} = \hat{y}_t + \Delta T \cdot \hat{v}_t \qquad (2)$$

$$\hat{v}_{t+1} = \hat{v}_t \qquad (3)$$

$$\hat{y}_t = \hat{y}_{t-1} + \alpha \cdot (y_t - \hat{y}_{t-1}) \qquad (4)$$

$$\hat{v}_t = \hat{v}_{t-1} + \frac{\beta}{\Delta T} \cdot (y_t - \hat{y}_{t-1}) \qquad (5)$$

wherein the equations (2) and (3) represent the predictive phase and the equations (4) and (5) represent the corrective phase, the variables in the equations represent estimates of the respective measured variable and the scanning time between two successive measurements, the index t indicates the current value with respect to the current measurement, the index t−1 indicates the value with respect to the respective last measurement, the index t−1 indicates the value with respect to the respective next measurement, and filter characteristics are adjustable via a parameter $\alpha$ and a parameter $\beta$.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
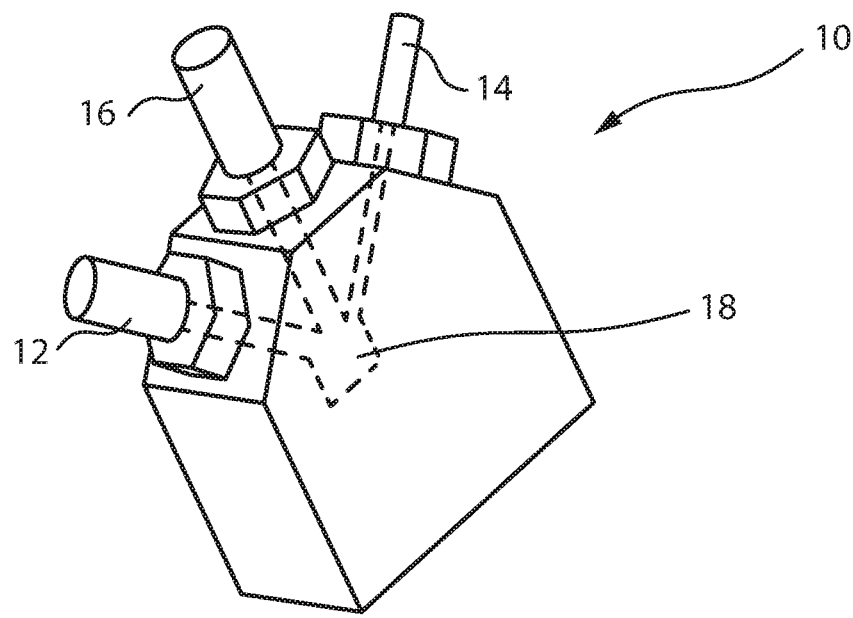
FIG. 1 simplifies an apparatus for mixing dialysate in advance as a component installable in an apparatus for extracorporeal blood treatment according to a first embodiment.
Figure 2:
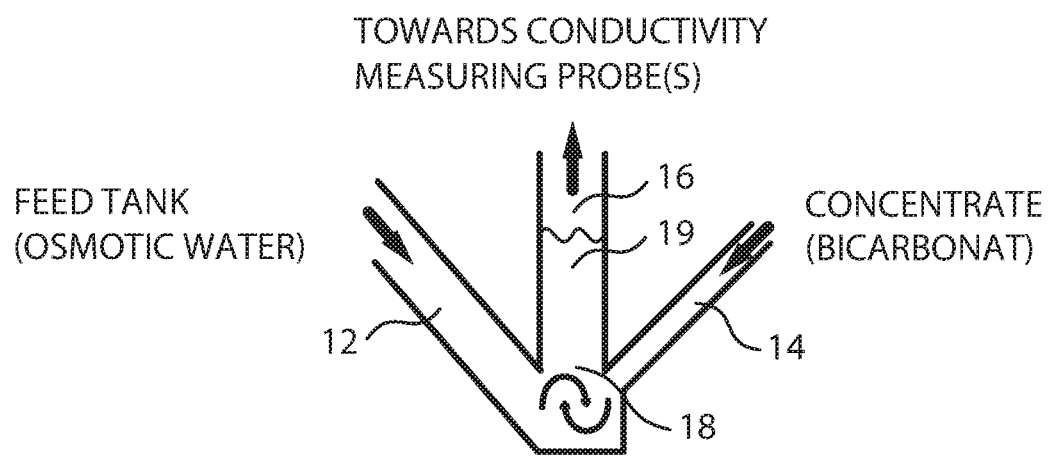
FIG. 2 shows a schematic diagram of premixing dialysate in the apparatus for mixing dialysate in advance according to the first embodiment.

It is noted that in the drawing like or equally acting elements and components are denoted with the same reference numerals and are not redundantly described.

FIG. 1 simplifies a premixing apparatus 10 for mixing dialysate in advance as a component installable in an apparatus for extracorporeal blood treatment, such as e.g. a dialysis machine, according to a first embodiment. The concept of premixing underlying in this case has to fulfil two objects, on the one hand premixing the concentrates with the osmotic water and, on the other hand, preventing the concentrates, especially bicarbonate, from outgassing.

According to the present embodiment, the premixing apparatus 10 includes a first feed 12 for supplying (quantity-controlled on the machine side) the osmotic water heated in a feed tank (not shown), a second feed 14 for supplying (quantity-controlled on the machine side) at least one concentrate directly from a rotary slide piston pump (not shown) of the apparatus for extracorporeal blood treatment and a drain 16 for draining the premixed dialysate from the premixing apparatus 10 and passing or supplying the premixed dialysate by or to at least one conductivity probe (not shown).

In a premixing portion 18 of the premixing apparatus 10 mixing or premixing of the osmotic water as a first fluid with the at least one concentrate as a second fluid in the counter flow principle, i.e. turbulently while swirling the osmotic water flowing in from a first direction via the first feed 12 into the premixing portion 18 and the at least one concentrate flowing in from a second direction via the second feed 14 takes place.

A water column 19 standing above the premixing portion 18 in the drain 16 prevents the concentrates, especially the bicarbonate, from outgassing.

Premixed dialysate drained from the drain 16 is supplied to at least one conductivity measuring cell or probe (not shown) which measures the premixed dialysate with respect to its conductivity and generates a conductivity measuring signal capable of being further processed.

It is understood that the afore-described premixing apparatus 10 is not limited to the shape or number of ports or inlets and outlets shown by way of example in the first embodiment. Furthermore, in an apparatus for extracorporeal blood treatment one or more premixing apparatus(es) 10 may be provided and arranged. A preferred arrangement of the premixing apparatus(es) 10 may be provided, for example, inside the machine on a carrier at a distance from fluid reservoirs and/or pump devices permitting the manufacture of the required fluid connections.

Figure 3A:
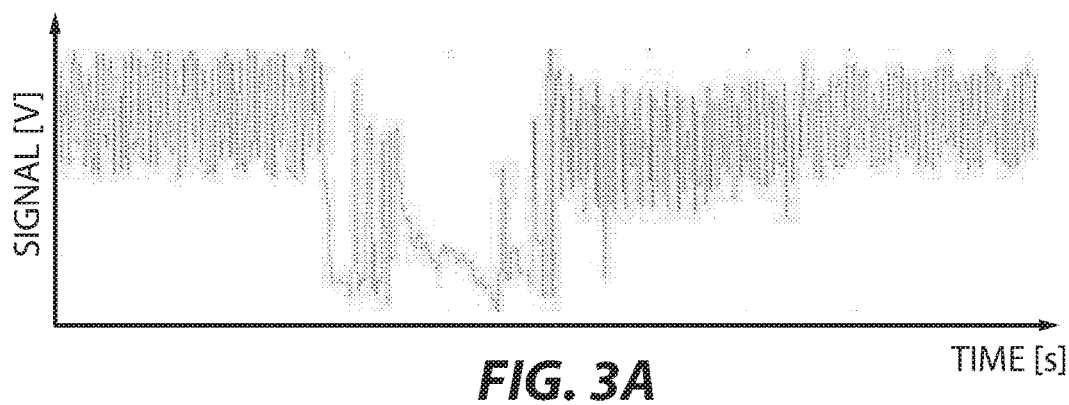
FIGS. 3A and 3B show diagrams of a curve of conductivity measuring signals before and after filtering, respectively, obtained by way of example.
Figure 3B:
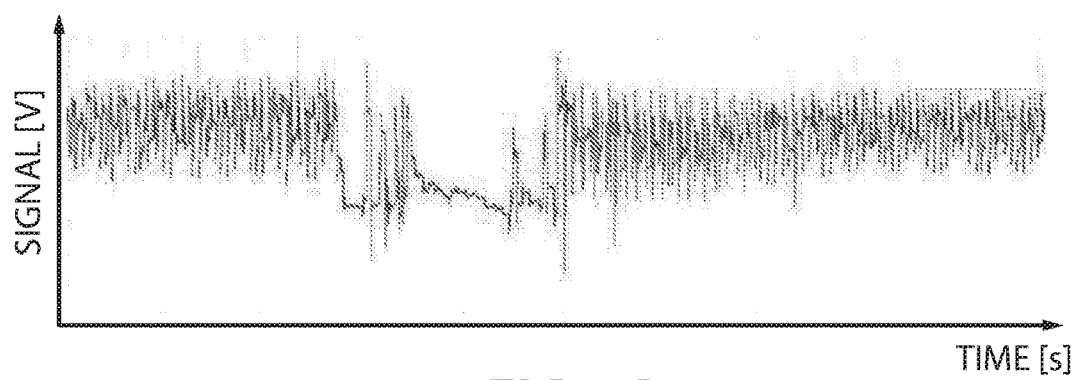

FIGS. 3A and 3B show diagrams of a process of conductivity measuring signals (a voltage in volt for example) obtained by way of example over a period T (for example in seconds). As can be inferred from FIG. 3A, the originally detected conductivity measuring signal is significantly noisy. In previously known and used filter methods it cannot be used for a stable control.

Therefore, initially the measuring variables can be freed from perturbations impacting to a lower degree by forming an average or forming a sliding average, for example. A resulting filtered conductivity signal, for example, is shown in FIG. 3B.

If the filtering effect is to be stronger, the degree of the filter may be increased. Although more complex types of filtering, such as e.g. a FIR filter or an IIR filter, have a better filtering effect while having a higher degree, they entail a significant delay for the overall system. The delay is directly proportional to the degree of the filter and thus grows equally proportional to the filter effect. In addition, types of filters such as an IIR filter provide no stationary impulse response so that within some ranges an application is impeded or even impossible.

Although in complex filter algorithms such as e.g. a Caiman filter the results are properly filtered, however, such filtering requires a more exact system description in the form of a state model. A state model in turn is not feasible for more complex systems such as a dialysis machine, for example. In addition, complicated calculating operations including matrices become necessary which substantially increase the required calculating capacity and render the parameterization of the filter more complicated.

An alternative to the aforementioned filter techniques is represented by a digital alpha-beta filter so called due to parameters $\alpha$, $\beta$ used (or designated) according to a second embodiment. An alpha-beta filter in this embodiment is a predictive algorithm which represents a simplified observer for a prognosis. The alpha-beta filter is based on an assumption to the effect that a process can be unambiguously determined by two state variables, wherein one of the state variables may be derived from the respective other one.

According to the present embodiment, this assumption is fulfilled by a state vector which is composed of the position (y) and the velocity (v):

$$v = \frac{dy}{dt} = \dot{y} \tag{1}$$

Then the filter algorithm is composed of two phases, a first predictive phase and a second corrective phase. In the first predictive phase, the next system state is determined by way of measured values. In the second corrective phase, the preceding determination is corrected by way of previous values.

The two afore-mentioned phases of the algorithm can be summarized in the following equations:

$$\hat{y}_{t+1} = \hat{y}_t + \Delta T \cdot \hat{v}_t \tag{2}$$

$$\hat{v}_{t+1} = \hat{v}_t \tag{3}$$

$$\hat{y}_t = \hat{y}_{t-1} + \alpha \cdot (y_t - \hat{y}_{t-1}) \tag{4}$$

$$\hat{v}_t = \hat{v}_{t-1} + \frac{\beta}{\Delta T} \cdot (y_t - \hat{y}_{t-1}) \tag{5}$$

wherein the equations (2) and (3) represent the predictive phase and the equations (4) and (5) represent the corrective phase.

The variables in the equations denote estimated values of the measured variable and of the scanning time between two sequential or successive measurements. The index t indicates the current value with respect to the current measurement, the index t−1 indicates the value with respect to the last measurement and the index t+1 indicates the value with respect to the next measurement. The two parameters α and β are used for adjusting the filter characteristics. Said parameters α and β should be selected within the range of from 0 to 1, if possible, so as to suppress interferences.

As afore-described, the aforementioned alpha-beta filter is based on the assumption that a process can be unambiguously determined by two state variables and in the filter alpha is corresponding to the distance and beta is corresponding to the velocity. The invention is not limited to such alpha-beta filter having two state variables or phases, however.

The alpha-beta filter can be basically expanded in any way and for example by another equation representing the acceleration. If the acceleration is denoted, for example, by gamma, in the expanded form an alpha-beta-gamma filter can be represented. Such alpha-beta-gamma filter can advantageously provide an even further improved filtering effect, while the calculating effort is justifiably increased.

By appropriately adding further equations and thus further phases of the filter according to the afore-mentioned principle, in modifications expansions may become arbitrarily comprehensive, wherein the use or applicability of an expansion may be merely dependent on the application. In other words, it is only dependent, from case to case, on an application, whether an expansion is taken into account.

Figure 4A:
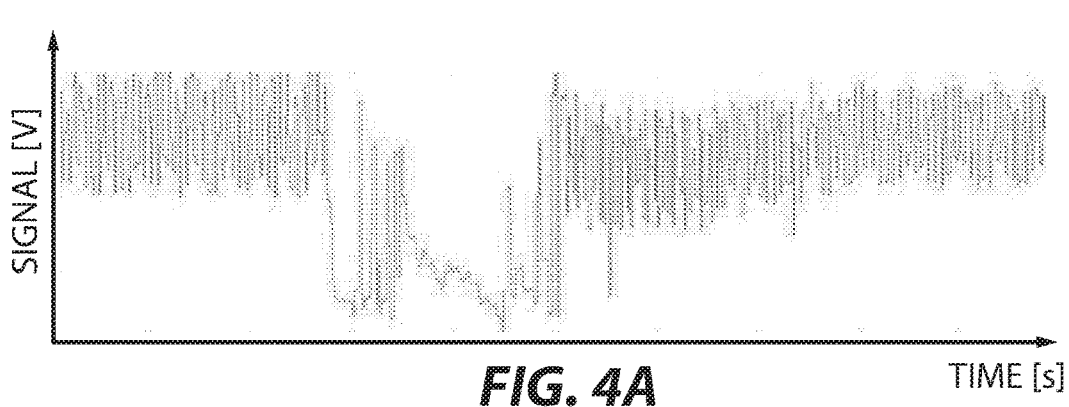
FIGS. 4A and 4B show diagrams of conductivity measuring signals before and after processing, respectively, while using a filter algorithm according to a second embodiment.
Figure 4B:
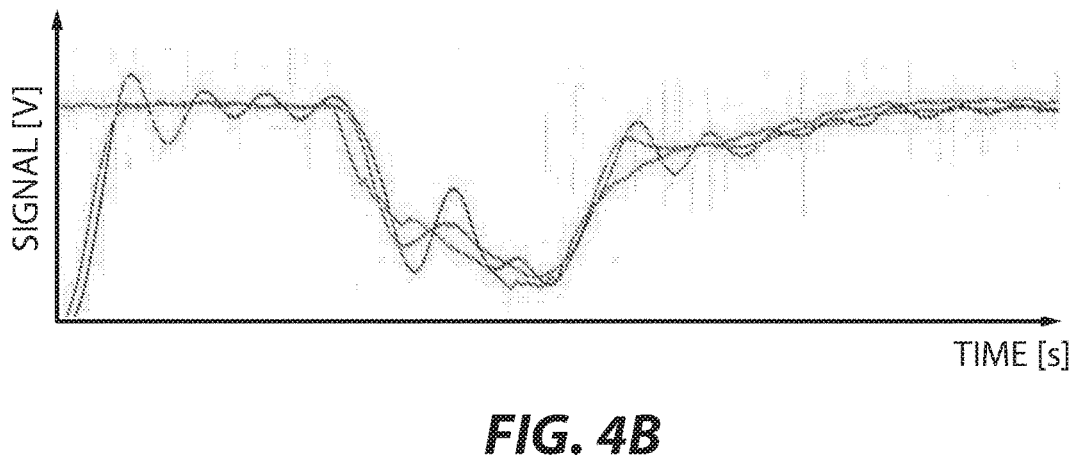

FIGS. 4A and 4B show, starting from the originally detected signal curve (FIG. 4A) a diagram of conductivity measuring signals after processing while using the filter algorithm according to the second embodiment (FIG. 4B).

The initial measuring values (in this case corresponding to FIG. 3A, for example) were processed for this purpose with the aid of the afore-described filter or filter algorithm and in FIG. 4B are shown as the smoothest one in total of the measuring value process curves which extends almost constant in the left-side initial area. Furthermore, in FIG. 4B, for illustrating the efficiency of the filter two comparative curves of each of a FIR low-pass filter and an IIR low-pass filter are shown each having overshoots and undershoots about a measuring value curve processed by the filter according to the present embodiment.

As afore-described, an apparatus for premixing fluids to form dialysate for an extracorporeal blood treatment comprises at least a first feed portion for supplying at least a first fluid from at least a first fluid reservoir, at least a second feed portion for supplying at least a second fluid from at least a second fluid reservoir, a premixing portion which is configured to premix fluids supplied via the feed portions in the counter flow into a fluid mixture, and at least one drain portion for draining the fluid mixture premixed in the premixing portion as the dialysate, and a method performs appropriate steps. In a conductivity measurement along the drain portion the conductivity of the premixed fluid mixture is measured with a digital filter adapted to be parameterized based on two state variables of the premixing process in two phases with a first predictive phase and a second corrective phase.

In the foregoing, the invention has been described by way of preferred embodiments. It is understood that details of the described preferred embodiments do not restrict the invention as such and various changes, modifications and/or equivalents all of which as such are within the scope of the invention defined by the enclosed claims may obviously result for those skilled in the art.

The invention claimed is:

1. An apparatus for premixing fluids to form a dialysate for an extracorporeal blood treatment, comprising:
   at least a first feed portion for supplying at least a first fluid from at least a first fluid reservoir;
   at least a second feed portion for supplying at least a second fluid from at least a second fluid reservoir;
   a premixing portion which is configured to premix the first and second fluids supplied via the first and second feed portions in counter flow to form a fluid mixture;
   at least one drain portion for draining the fluid mixture premixed in the premixing portion as the dialysate; and
   at least one conductivity measuring device along the at least one drain portion for measuring the conductivity of the premixed fluid mixture and to generate a conductivity measuring signal,
   wherein the at least one conductivity measuring device comprises a digital filter adjustable on the basis of at least two state variables of the premixing process,
   wherein one of the at least two state variables is derived from a respective other one and the digital filter is configured to be at least two-phase comprising a first predictive phase in which a next system state is determined by way of measured values and a second corrective phase in which the preceding determining is corrected by way of previous values.

2. The apparatus according to claim 1, wherein the at least a first fluid is osmotic water and the at least a second fluid is a concentrate of a substance to be used for the extracorporeal blood treatment.

3. The apparatus according to claim 2, wherein the concentrate is a bicarbonate concentrate.

4. The apparatus according to claim 1, wherein in the at least one drain portion a fluid column for generating a constant primary pressure is provided which is configured to prevent at least one of the supplied first and second fluids from outgassing.

5. The apparatus according to claim 1, wherein the at least one first feed portion and the at least one second feed portion are arranged with respect to the apparatus on an outside and the at least one drain portion is arranged between the at least one first feed portion and the at least one second feed portion and the first and second feed portions are connected to the premixing portion in a fluid-guiding manner so that the at least one first fluid flows from a first direction into the premixing portion and the at least one second fluid flows from a second direction into the premixing portion, and the at least one first feed portion and the at least one second feed portion adopt a predetermined angle with each other which is configured so that the counter-flow premixing of the fluids is generated in the premixing portion in a turbulent and automatic way based on flow.

6. The apparatus according to claim 1, wherein the at least two state variables form a state vector $$v = \frac{dy}{dt} = \dot{y} \quad (1)$$

wherein y represents a position and v represents a velocity and the first and second phases of the filter are determined by the equations:

$$\hat{y}_{t+1} = \hat{y}_t + \Delta T \cdot \hat{v}_t \quad (2)$$

$$\hat{v}_{t+1} = \hat{v}_t \quad (3)$$

$$\hat{y}_t = \hat{y}_{t-1} + \alpha \cdot (y_t - \hat{y}_{t-1}) \quad (4)$$

$$\hat{v}_t = \hat{v}_{t-1} + \frac{\beta}{\Delta T} \cdot (y_t - \hat{y}_{t-1}) \quad (5)$$

wherein the equations (2) and (3) represent the predictive phase and the equations (4) and (5) represent the corrective phase, the variables in the equations represent estimates of the respectively measured variable and the scanning time between two successive measurements, the index t indicates the current value with respect to the current measurement, the index t−1 indicates the value with respect to the respective last measurement, the index t+1 indicates the value with respect to the respective next measurement, and filter characteristics are adjustable via a parameter α and a parameter β.

7. A method for premixing fluids to form dialysate for an extracorporeal blood treatment, comprising the steps of:

supplying at least a first fluid from at least a first fluid reservoir via at least a first feed portion;

supplying at least a second fluid from at least a second fluid reservoir via at least a second feed portion;

premixing the first and second fluids supplied via the first and second feed portions in counter flow to form a fluid mixture in a premixing portion;

draining the fluid mixture premixed in the premixing portion as the dialysate via at least one drain portion; and performing a conductivity measurement along the at least one drain portion for measuring the conductivity of the premixed fluid mixture for generating a conductivity measuring signal, wherein the conductivity measurement is performed by a digital filter which is adjustable on the basis of at least two state variables of the premixing process in two phases with a first predictive phase and a second corrective phase.

8. The method according to claim 7, wherein the two state variables form a state vector $$v = \frac{dy}{dt} = \dot{y} \quad (1)$$

wherein y represents a position and v represents a velocity, and the first and second phases of the filter are determined by the equations:

$$\hat{y}_{t+1} = \hat{y}_t + \Delta T \cdot \hat{v}_t \quad (2)$$

$$\hat{v}_{t+1} = \hat{v}_t \quad (3)$$

$$\hat{y}_t = \hat{y}_{t-1} + \alpha \cdot (y_t - \hat{y}_{t-1}) \quad (4)$$

$$\hat{v}_t = \hat{v}_{t-1} + \frac{\beta}{\Delta T} \cdot (y_t - \hat{y}_{t-1}) \quad (5)$$

wherein the equations (2) and (3) represent the predictive phase and the equations (4) and (5) represent the corrective phase, the variables in the equations represent estimates of the respectively measured variable and the scanning time between two successive measurements, the index t indicates the current value with respect to the current measurement, the index t−1 indicates the value with respect to the respective last measurement, the index t+1 indicates the value with respect to the respective next measurement, and filter characteristics are adjustable via a parameter α and a parameter β.

* * * * *